United States Patent
Louie et al.

(10) Patent No.: US 7,747,477 B1
(45) Date of Patent: Jun. 29, 2010

(54) PHARMACY SUPPLY TRACKING AND STORAGE SYSTEM

(75) Inventors: Shelton Louie, Vancouver, WA (US); Stephen A. Garrett, Vancouver, WA (US)

(73) Assignee: GSL Solutions, Inc., Vancouver, WA (US)

(*) Notice: Subject to any disclaimer, the term of this patent is extended or adjusted under 35 U.S.C. 154(b) by 1177 days.

(21) Appl. No.: 10/928,756

(22) Filed: Aug. 26, 2004

Related U.S. Application Data

(63) Continuation-in-part of application No. 09/715,439, filed on Nov. 16, 2000, and a continuation-in-part of application No. 09/829,536, filed on Apr. 9, 2001, now abandoned, and a continuation-in-part of application No. 09/991,529, filed on Nov. 16, 2001, now Pat. No. 7,496,521, and a continuation-in-part of application No. 09/991,249, filed on Nov. 16, 2001, now abandoned, and a continuation-in-part of application No. 09/991,530, filed on Nov. 16, 2001, now abandoned, and a continuation-in-part of application No. 10/223,336, filed on Aug. 18, 2002, now abandoned, and a continuation-in-part of application No. 10/223,308, filed on Aug. 18, 2002, and a continuation-in-part of application No. 10/925,221, filed on Aug. 23, 2004, now abandoned.

(60) Provisional application No. 60/496,940, filed on Aug. 21, 2003.

(51) Int. Cl.
G06Q 10/00 (2006.01)
G06G 1/14 (2006.01)
G06F 19/00 (2006.01)

(52) U.S. Cl. ............................ 705/28; 705/22; 235/385

(58) Field of Classification Search ............... 705/28
See application file for complete search history.

(56) References Cited

U.S. PATENT DOCUMENTS 404,458 A    6/1889   Woodruff
541,111 A    6/1895   McDonald (Continued)

FOREIGN PATENT DOCUMENTS

EP     0 899 677     3/1999

(Continued)

OTHER PUBLICATIONS

White, Ron, How Computers Work, Millenium Ed., Que Corporation, Sep. 22, 1999.

(Continued)

*Primary Examiner*—F. Ryan Zeender
*Assistant Examiner*—Faris Almatrahi
(74) *Attorney, Agent, or Firm*—Harness Dickey & Pierce, P.L.C.

(57) ABSTRACT

A pharmacy supply container tracking system that automatically detects and tracks a pharmacy supply container within a pharmacy is disclosed. In a preferred embodiment the system also detects and tracks prescription orders of customers, and automatically verifies that the correct pharmacy supply is used to fill a particular prescription order. One disclosed system includes using tags, such as Radio-Frequency Identification ("RFID") tags, and their related readers to locate objects through electromagnetic interrogation of a spatial region to determine the presence of an object within that special region.

6 Claims, 15 Drawing Sheets

U.S. PATENT DOCUMENTS

| | | |
|---|---|---|
| 827,649 A | 7/1906 | Murphy |
| 1,236,324 A | 8/1917 | Leonard |
| 1,592,497 A | 7/1926 | Mays |
| 1,750,291 A | 3/1930 | Whetstone |
| 1,993,477 A | 3/1935 | Glenn et al. |
| 2,174,068 A | 9/1939 | Citron |
| 2,962,335 A | 11/1960 | Benson |
| 3,167,873 A | 2/1965 | Toms |
| 3,172,711 A | 3/1965 | Gillotte |
| 3,744,867 A | 7/1973 | Shaw |
| 3,798,810 A | 3/1974 | Brisson et al. |
| 3,844,416 A | 10/1974 | Potter |
| 3,865,447 A | 2/1975 | Patterson |
| 3,942,851 A | 3/1976 | Kaplan |
| 3,970,010 A | 7/1976 | Cantley |
| 4,210,802 A | 7/1980 | Sakai |
| 4,653,818 A | 3/1987 | DeBruyn |
| 4,688,026 A | 8/1987 | Scribner et al. |
| 4,737,910 A | 4/1988 | Kimbrow |
| 4,746,830 A | 5/1988 | Holland |
| 4,766,542 A | 8/1988 | Pilarczyk |
| 4,793,495 A | 12/1988 | Preu |
| 4,993,558 A | 2/1991 | Assael |
| 5,047,948 A | 9/1991 | Turner |
| 5,079,006 A | 1/1992 | Urquhart |
| 5,160,048 A | 11/1992 | Leyden et al. |
| 5,208,762 A * | 5/1993 | Charhut et al. ............... 700/216 |
| 5,231,273 A | 7/1993 | Caswell et al. |
| 5,245,163 A | 9/1993 | Bar-Yehuda |
| 5,328,784 A | 7/1994 | Fukuda |
| 5,346,297 A | 9/1994 | Colson et al. |
| 5,389,919 A | 2/1995 | Warren et al. |
| 5,434,775 A | 7/1995 | Sims et al. |
| 5,481,546 A | 1/1996 | Dinkins |
| 5,495,250 A | 2/1996 | Ghaem et al. |
| 5,593,267 A | 1/1997 | McDonald et al. |
| 5,595,356 A | 1/1997 | Kewin |
| 5,597,995 A | 1/1997 | Williams et al. |
| 5,640,002 A | 6/1997 | Ruppert et al. |
| 5,646,389 A | 7/1997 | Bravman et al. |
| 5,646,592 A | 7/1997 | Tuttle |
| 5,689,238 A | 11/1997 | Cannon et al. |
| 5,700,998 A | 12/1997 | Palti |
| 5,771,657 A * | 6/1998 | Lasher et al. .................... 53/55 |
| 5,794,213 A | 8/1998 | Markman |
| 5,797,515 A | 8/1998 | Liff et al. |
| 5,798,693 A | 8/1998 | Engellenner |
| 5,805,456 A | 9/1998 | Higham et al. |
| 5,838,253 A | 11/1998 | Wurz et al. |
| 5,845,264 A | 12/1998 | Nellhaus |
| 5,907,493 A | 5/1999 | Boyer et al. |
| 5,926,093 A | 7/1999 | Bowers et al. |
| 5,936,527 A | 8/1999 | Isaacman et al. |
| 5,963,132 A | 10/1999 | Yoakum |
| 5,974,393 A | 10/1999 | McCullough et al. |
| 5,996,889 A | 12/1999 | Fuchs et al. |
| 6,008,727 A | 12/1999 | Want et al. |
| 6,021,392 A | 2/2000 | Lester et al. |
| 6,057,756 A | 5/2000 | Engellenner |
| 6,057,764 A | 5/2000 | Williams |
| 6,098,892 A | 8/2000 | Peoples |
| 6,116,505 A | 9/2000 | Withrow |
| 6,150,942 A | 11/2000 | O'Brien |
| 6,170,746 B1 | 1/2001 | Brook et al. |
| 6,202,923 B1 | 3/2001 | Boyer et al. |
| 6,209,978 B1 | 4/2001 | Khan |
| 6,219,587 B1 | 4/2001 | Ahlin et al. |
| 6,223,137 B1 | 4/2001 | McCay et al. |
| 6,232,876 B1 | 5/2001 | Maloney |
| 6,245,057 B1 | 6/2001 | Sieben et al. |
| 6,249,212 B1 | 6/2001 | Beigel et al. |
| 6,259,654 B1 | 7/2001 | de la Huerga |
| 6,294,999 B1 | 9/2001 | Yarin et al. |
| 6,318,536 B1 | 11/2001 | Korman et al. |
| 6,324,522 B2 | 11/2001 | Peterson et al. |
| 6,339,732 B1 | 1/2002 | Phoon et al. |
| 6,354,493 B1 | 3/2002 | Mon |
| 6,357,662 B1 | 3/2002 | Helton et al. |
| 6,366,206 B1 | 4/2002 | Ishikawa et al. |
| 6,366,220 B1 | 4/2002 | Elliott |
| 6,380,858 B1 | 4/2002 | Yarin et al. |
| 6,392,544 B1 | 5/2002 | Collins et al. |
| 6,415,295 B1 | 7/2002 | Feinberg |
| 6,415,978 B1 | 7/2002 | McAllister |
| 6,430,268 B1 | 8/2002 | Petite |
| 6,440,069 B1 | 8/2002 | Raymond et al. |
| 6,448,886 B2 | 9/2002 | Garber et al. |
| 6,450,406 B2 | 9/2002 | Brown |
| 6,464,142 B1 | 10/2002 | Denenberg et al. |
| 6,496,806 B1 | 12/2002 | Horwitz et al. |
| 6,502,005 B1 | 12/2002 | Wrubel et al. |
| 6,522,945 B2 | 2/2003 | Sleep et al. |
| 6,529,786 B1 | 3/2003 | Sim |
| 6,557,758 B1 | 5/2003 | Monico |
| 6,564,121 B1 | 5/2003 | Wallace et al. |
| 6,611,806 B1 | 8/2003 | Harvey |
| 6,648,153 B2 | 11/2003 | Holmes |
| 6,714,121 B1 | 3/2004 | Moore |
| 6,758,403 B1 | 7/2004 | Keys et al. |
| 6,763,996 B2 | 7/2004 | Rakers et al. |
| 6,769,228 B1 | 8/2004 | Mahar |
| 6,877,658 B2 | 4/2005 | Raistrick et al. |
| 6,935,560 B2 | 8/2005 | Andreasson et al. |
| 6,995,675 B2 | 2/2006 | Curkendall et al. |
| 7,142,118 B2 | 11/2006 | Hamilton et al. |
| 7,148,803 B2 | 12/2006 | Bandy et al. |
| 7,158,030 B2 | 1/2007 | Chung |
| 7,175,081 B2 | 2/2007 | Andreasson et al. |
| 7,289,015 B2 | 10/2007 | Moyer |
| 7,382,263 B2 | 6/2008 | Danowski et al. |
| 2001/0017817 A1 | 8/2001 | de la Huerga |
| 2001/0040512 A1 | 11/2001 | Hines et al. |
| 2002/0132226 A1 | 9/2002 | Nair et al. |
| 2002/0180588 A1 | 12/2002 | Erickson et al. |
| 2003/0086338 A1 | 5/2003 | Sastry et al. |
| 2003/0191430 A1 | 10/2003 | D'Andrea et al. |
| 2003/0200726 A1 | 10/2003 | Rast |
| 2004/0036623 A1 | 2/2004 | Chung |
| 2005/0237201 A1 | 10/2005 | Nedblake |
| 2006/0190628 A1 | 8/2006 | Linton et al. |

FOREIGN PATENT DOCUMENTS

| | | |
|---|---|---|
| EP | 1 049 042 | 11/2000 |

OTHER PUBLICATIONS

Derfler, Frank J. et al., How Networks Work, Millenium Ed., Que Corporation, Aug. 23, 2000.

Gralla, Preston, How the Internet Works, Millenium Ed., Que Corporation, Sep. 23, 1999.

* cited by examiner

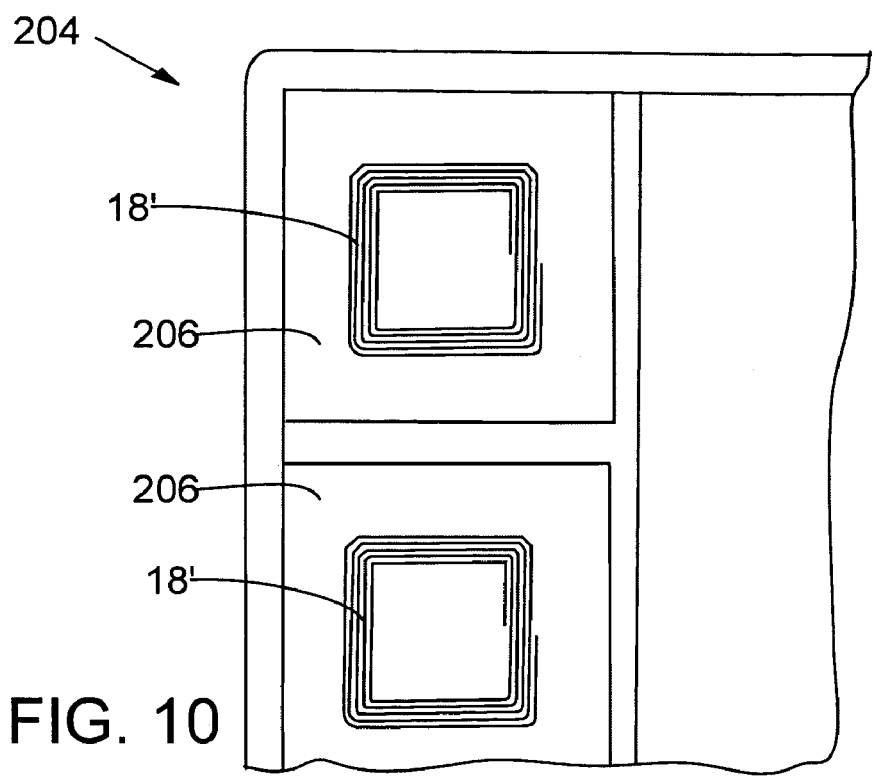
FIG. 10
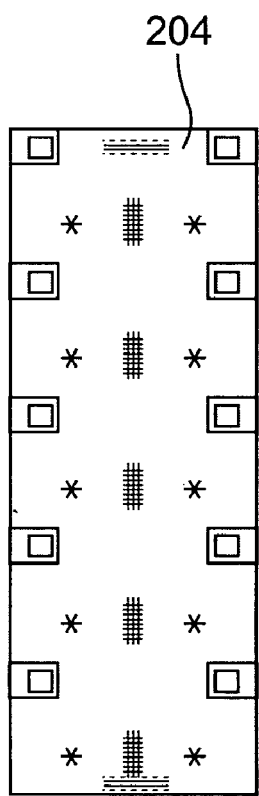  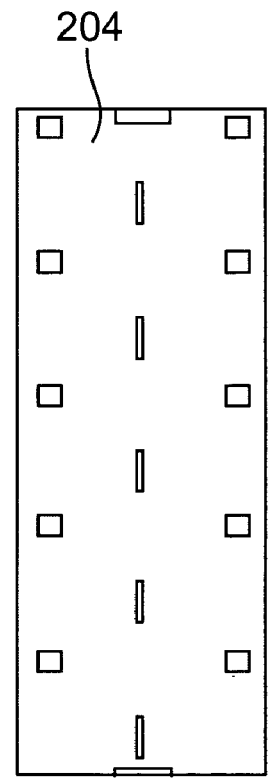
FIG. 11A    FIG. 11B    FIG. 11C

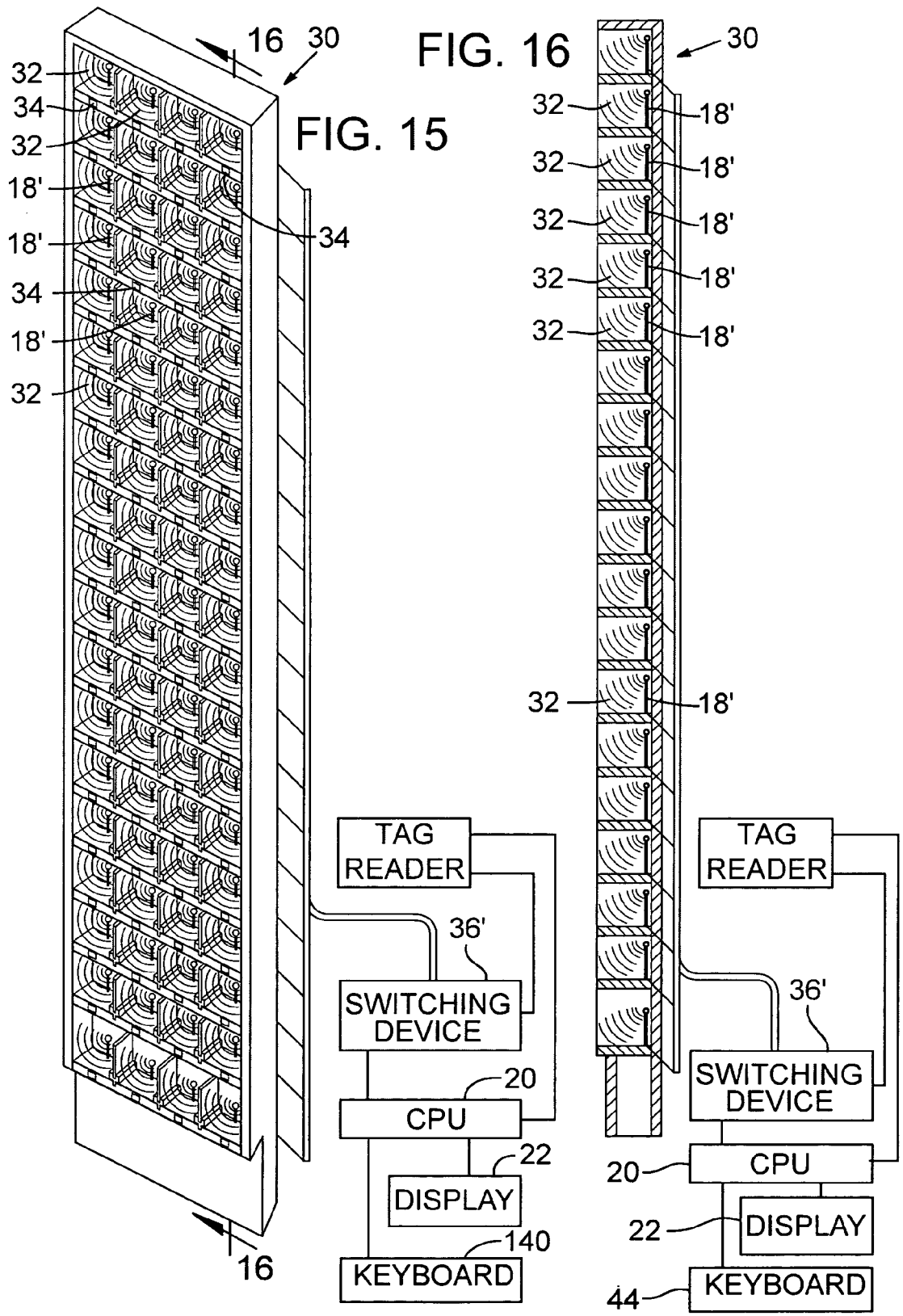

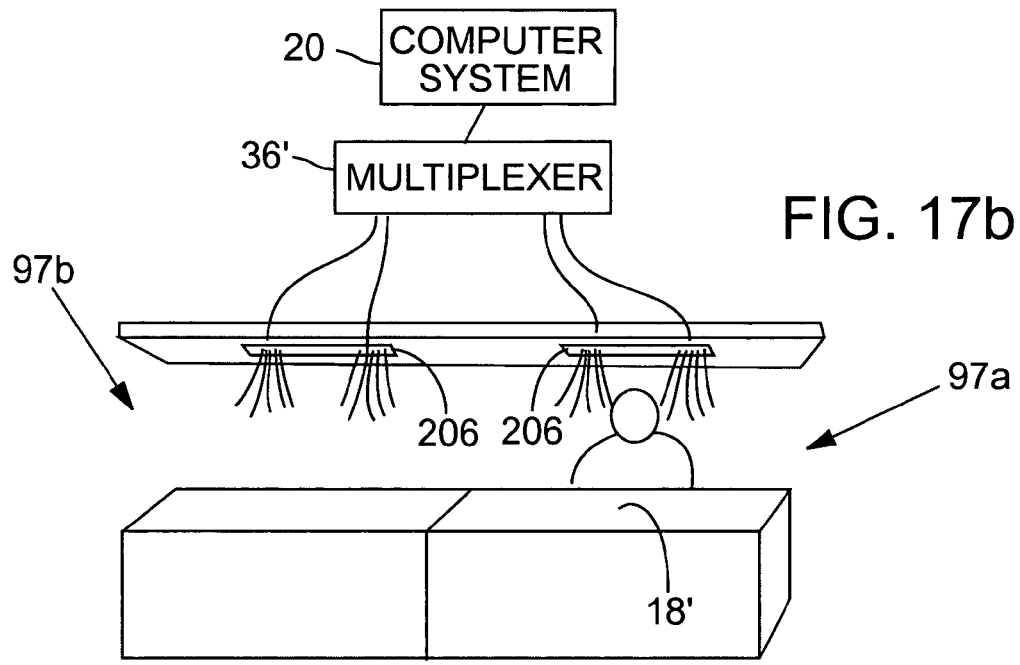
FIG. 17b
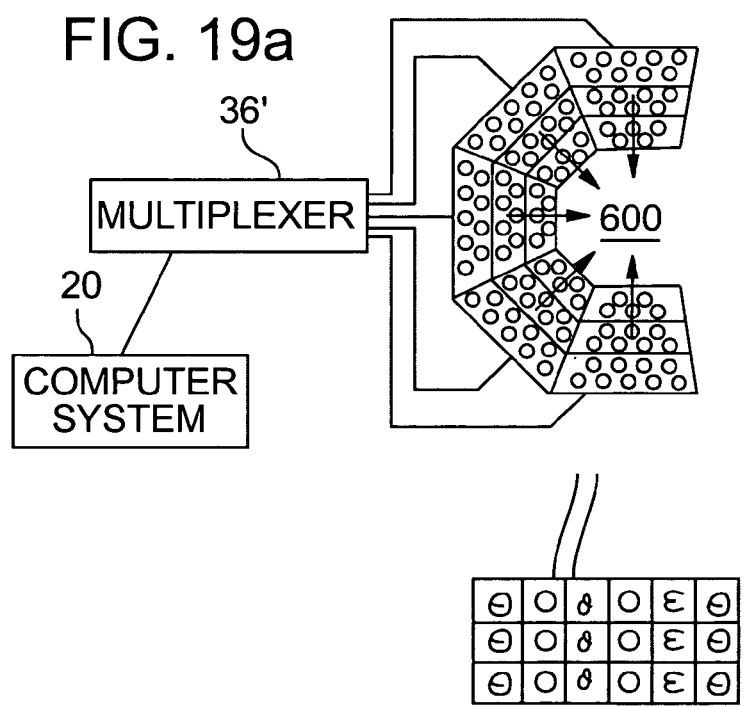
FIG. 19a
FIG. 19b

US 7,747,477 B1

PHARMACY SUPPLY TRACKING AND STORAGE SYSTEM

This application is a continuation-in-part of U.S. patent application Ser. No. 09/715,439, filed on Nov. 16, 2000, Ser. No. 09/829,536, filed on Apr. 9, 2001, now abandoned; Ser. No. 09/991,529, filed on Nov. 16, 2001, now U.S. Pat. No. 7,496,521; Ser. No. 09/991,249, filed on Nov. 16, 2001, now abandoned; Ser. No. 09/991,530, filed on Nov. 16, 2001, now abandoned; Ser. No. 10/223,336, filed on Aug. 18, 2002, now abandoned; Ser. No. 10/223,308, filed on Aug. 18, 2002, now pending, and Ser. No. 10/925,221, filed on Aug. 23, 2004 now abandoned, the disclosures of which are hereby incorporated by reference. This application also claims priority to U.S. Provisional Patent Application Ser. No. 60/496,940 filed on Aug. 21, 2003.

FIELD OF THE INVENTION

The present invention relates to a pharmacy supply tracking and storage system. In particular, it automatically detects and tracks supplies within a pharmacy thereby aiding inventory tracking and location of these materials.

BACKGROUND OF THE INVENTION

Pharmaceutical medications increase the lives and the quality of lives of millions of people. Moreover, as the general population ages and new beneficial drugs are introduced, prescription order volumes to be filled at pharmacies and distributed to individual customers and through health care providers such as hospitals, convalescent centers, and the like, are expected to double within the next few years. This present and expected increase in order volume places enormous pressure on pharmacists, other pharmacy workers, and health care providers, who strive to fill and distribute each order efficiently, accurately and quickly.

The process of retrieving, filling, and distributing a prescription order to a patient or customer can include many different people and organizations performing numerous tasks. An error with any one of these tasks can lead to the mishandling of a patient's prescription order. Such mishandling of a prescription order often results in a patient not timely receiving their prescription order or receiving a wrong, possibly even deadly, prescription order or the like.

Timely and efficient filling of prescriptions is maximized when a pharmacy worker can easily locate and retrieve supplies used for filling individual prescriptions. Unfortunately, these supplies are often misplaced within the pharmacy, or not replenished in a timely manner, thereby hindering the timely filling of prescription orders for customers and patients.

SUMMARY OF THE INVENTION

Despite the known pharmacy supply tracking and distribution systems, there remains a need for an economical, pharmacy supply tracking and distribution system that automatically detects the presence of a particular pharmacy supply and automatically tracks its movement throughout the pharmacy. In addition to other benefits that will become apparent in the following disclosure, the present invention fulfills these needs.

The present invention is a pharmacy supply tracking system that automatically detects and tracks a pharmacy supply within a pharmacy. In a preferred embodiment the system also detects and tracks prescription orders of customers, and automatically verifies that the correct pharmacy supply is used to fill a particular prescription order.

One such system includes using tags, such as Radio-Frequency Identification ("RFID") tags, and their related readers to locate objects through electromagnetic interrogation of a spatial region to determine the presence of an object within that special region. A unique tag is operably secured to each prescription order and each pharmacy supply, and tag readers, which are in communication with a computer system, are positioned at defined locations throughout the pharmacy, including within a first storage area for storing pharmacy supplies, to detect the presence of a tag within a defined physical location. Accordingly, the computer system correlates the prescription orders and pharmacy supplies with a database of information to allow both the prescription orders and pharmacy supplies to be tracked and located within the pharmacy.

Preferably, the first storage area includes a storage cabinet having a plurality of cubbies therein, with each cubby having its own tag reader. More preferably, the tag reader, which is in communication with a computer system, is operably secured to a multiplexer with a plurality of antennae extending therefrom. Each antenna is positioned at a particular cubby location. The multiplexer cycles through connecting each antenna such that all locations are scanned using the common tag reader.

Preferably, in situations where the antenna are in close proximity to each other, such as being in adjacent cubbies in the container, the antenna signals are shielded from each other, say for example, with a grounding circuit positioned therebetween. More preferably, a antenna are formed onto a substantially planar frame with a grounding circuit extending therearound, thereby directing the tag reading signal substantially perpendicular to the planar frame. Accordingly, the planar frame containing the antenna may be positioned substantially vertically adjacent to a storage bin in a pharmacy supply storage area, or positioned substantially horizontally under a worker's work area. Accordingly, the detectable field provided by the antenna can be limited to a very specific physical area within a work area filled with other tracked work areas positioned in very close proximity.

Additional objects and advantages of the present invention will be apparent from the detailed description of the preferred embodiment thereof, which proceeds with reference to the accompanying drawings.

BRIEF DESCRIPTION OF THE DRAWINGS

FIG. 10 is a top plan view of an exemplar, planar, antenna array card showing possible shielding encircling each antenna.

FIG. 11 is a top, side, and back view of the antenna array card of FIG. 10.

FIG. 15 is a front, isometric view of the storage structure of FIG. 14 showing a possible connection to a computing device.

FIG. 16 is a side view of the storage structure of FIG. 15.

FIG. 17b is an alternative exemplar, isometric view of a possible workstation having a substantially horizontally mounted planar frame containing at least one tag reader antenna therein.

FIG. 18 is a top view of the workstation of FIG. 17a.

FIG. 19a is a top view of an exemplar array of tag reading antenna directed to define a common scanning space or scanning tunnel.

FIG. 19b is a top view of an alternative exemplar array of tag reading antenna.

DETAILED DESCRIPTION OF PREFERRED EMBODIMENTS

A prescription order 12 and/or pharmacy supply 13 tracking and distribution system 10 having a pharmacy supply storage device with a plurality of individually-identified cubbies therein is disclosed in FIGS. 1-22.

Figure 5:
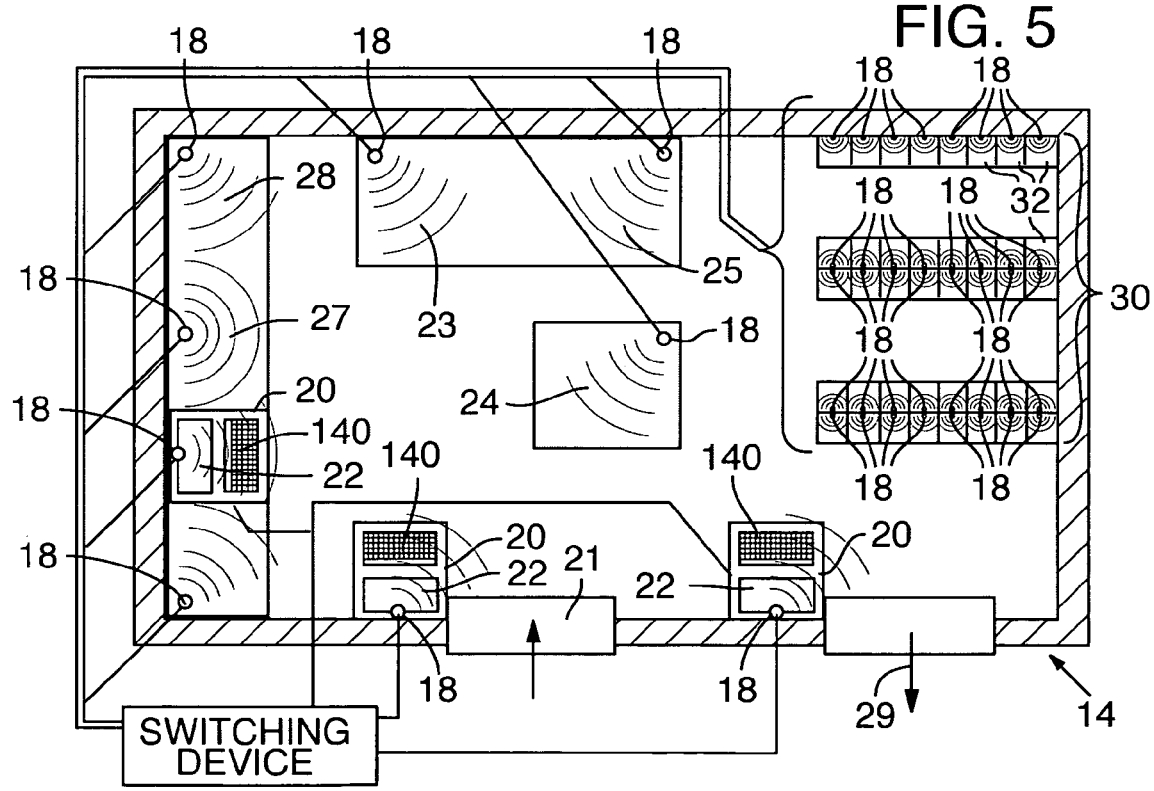
FIG. 5 is a schematic view of a prescription order tracking system used in a pharmacy in accordance with a preferred embodiment of the present invention.
Figure 6:
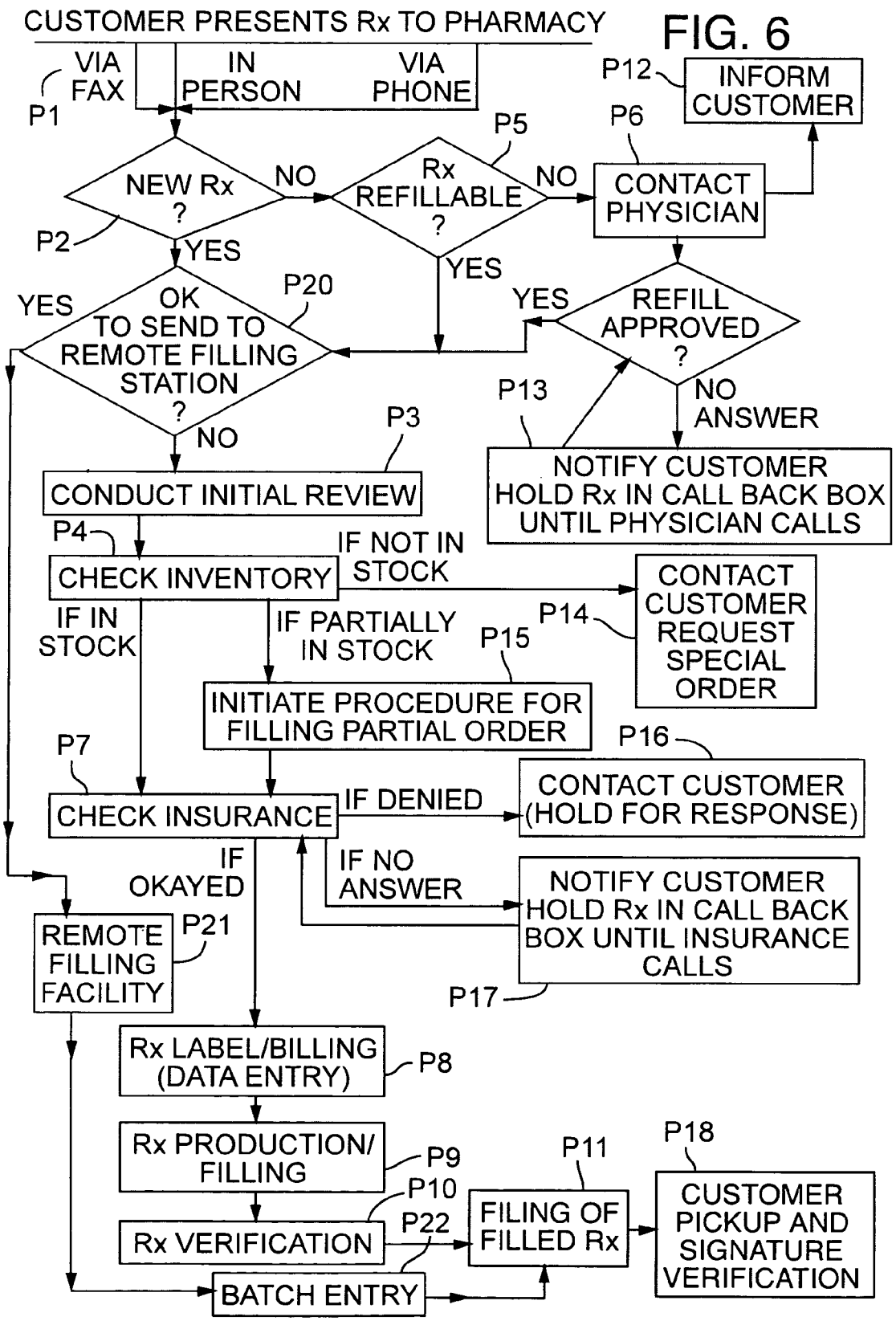
FIG. 6 is a block diagram of an exemplar pharmacy prescription order filling system showing a possible filling process.
Figure 7:
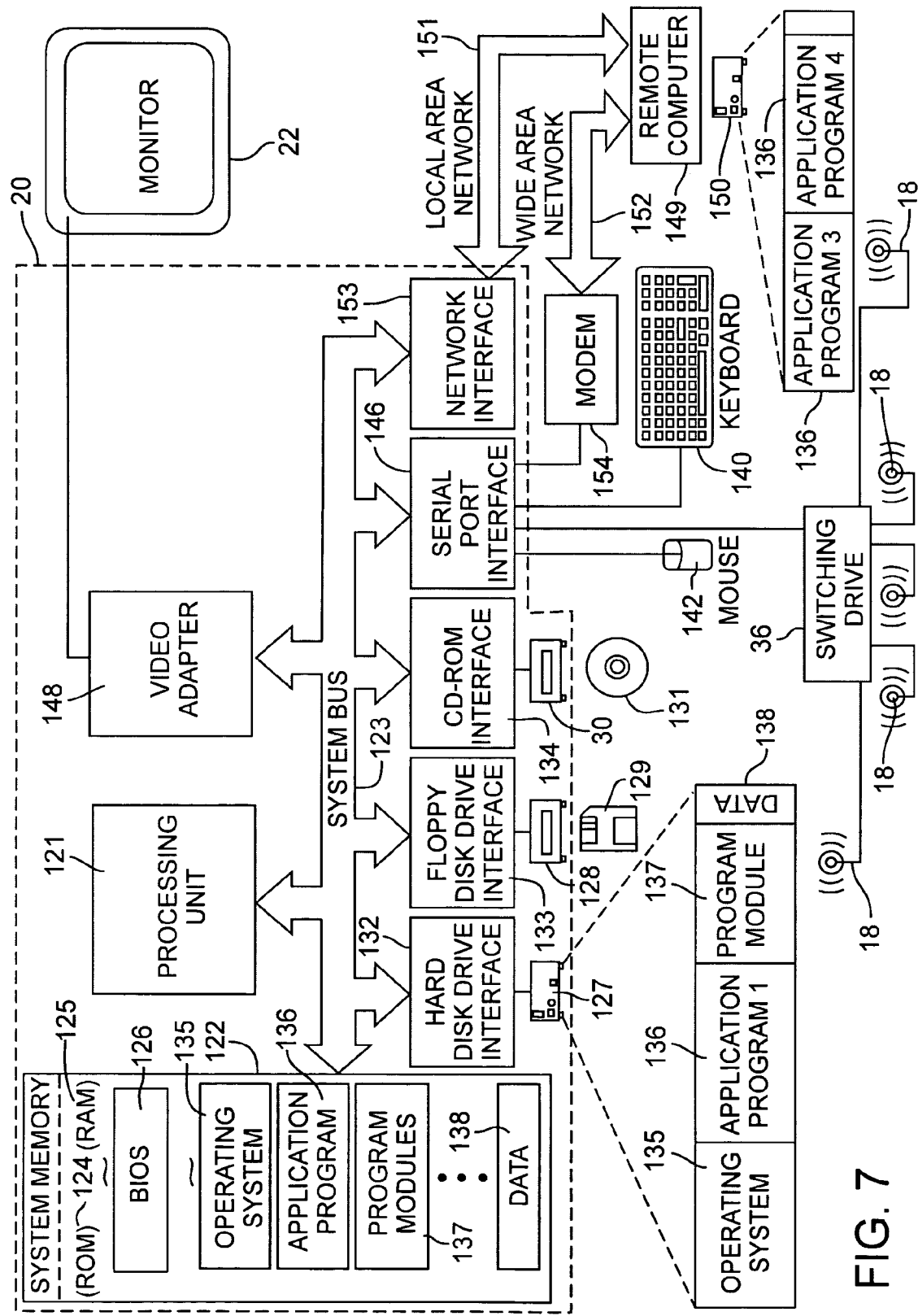
FIG. 7 is a block diagram of an exemplary computer system in accordance with a preferred embodiment of the present invention.

In general and as shown in FIGS. 5 & 6, a prescription order 12 is presented to the remote pharmacy 14 by a healthcare provider, customer or other agent (hereafter collectively referred to as a "healthcare provider") for a patient. Referring to FIG. 6, the pharmacy or the healthcare provider assigns an identification tag 16 to the prescription order 12. Tag reading devices 18 are positioned at key locations throughout the pharmacy 14 (FIG. 5) and the healthcare provider's facility 17 (FIG. 21) and in communication with a computer system 20 having a display 22, such that the movement of the prescription order 12 throughout the pharmacy 14 and/or the healthcare provider's facility 17 automatically detects and records the location of the tag 16 without further worker input.

A plurality of tags may be simultaneously tracked, thereby facilitating bulk processing and distribution of prescription orders, particularly those received from the off-site facility 15. Moreover, each tag preferably includes read-writable memory that is preferably coded with key information about the prescription order, such as the customer's name, identifying information, date of birth, social security number, prescribed drug, insurance information, directions for use, National Drug Control ("NDC") number, and the like. Accordingly, a pharmacy worker within the pharmacy, a worker at the healthcare provider's facility or even a worker at a third remote location can quickly and easily determine all relevant information about a particular prescription order without necessarily having to first correlate a tag identification code with a computer system database.

In addition, a worker can easily determine the location of the prescription order 12 or pharmacy supply 13 within the pharmacy and/or the healthcare provider's facility 17 by entering commands in the computer system 20 with a user input device such as a keyboard 120 to display the location of the prescription order 12 on the computer display 22. The individual elements forming the present invention are discussed in greater detail below.

A. Tags

Preferably, one or more tag readers 18 locate tags 16 through electromagnetic interrogation of a spatial region to determine the presence of an object. One such system is disclosed in U.S. Pat. No. 6,057,756 to Engellenner, the disclosure of which is hereby incorporated by reference. In general, the tag 16 is an electromagnetic antenna and/or signal receiver which responds either passively or actively to announce the presence (or absence) of an object within a controlled region defined by a broadcasted electromagnetic interrogation signal. Preferably, each tag 16 includes a coding mechanism for uniquely identifying it with respect to other tags in the system.

Figure 1:
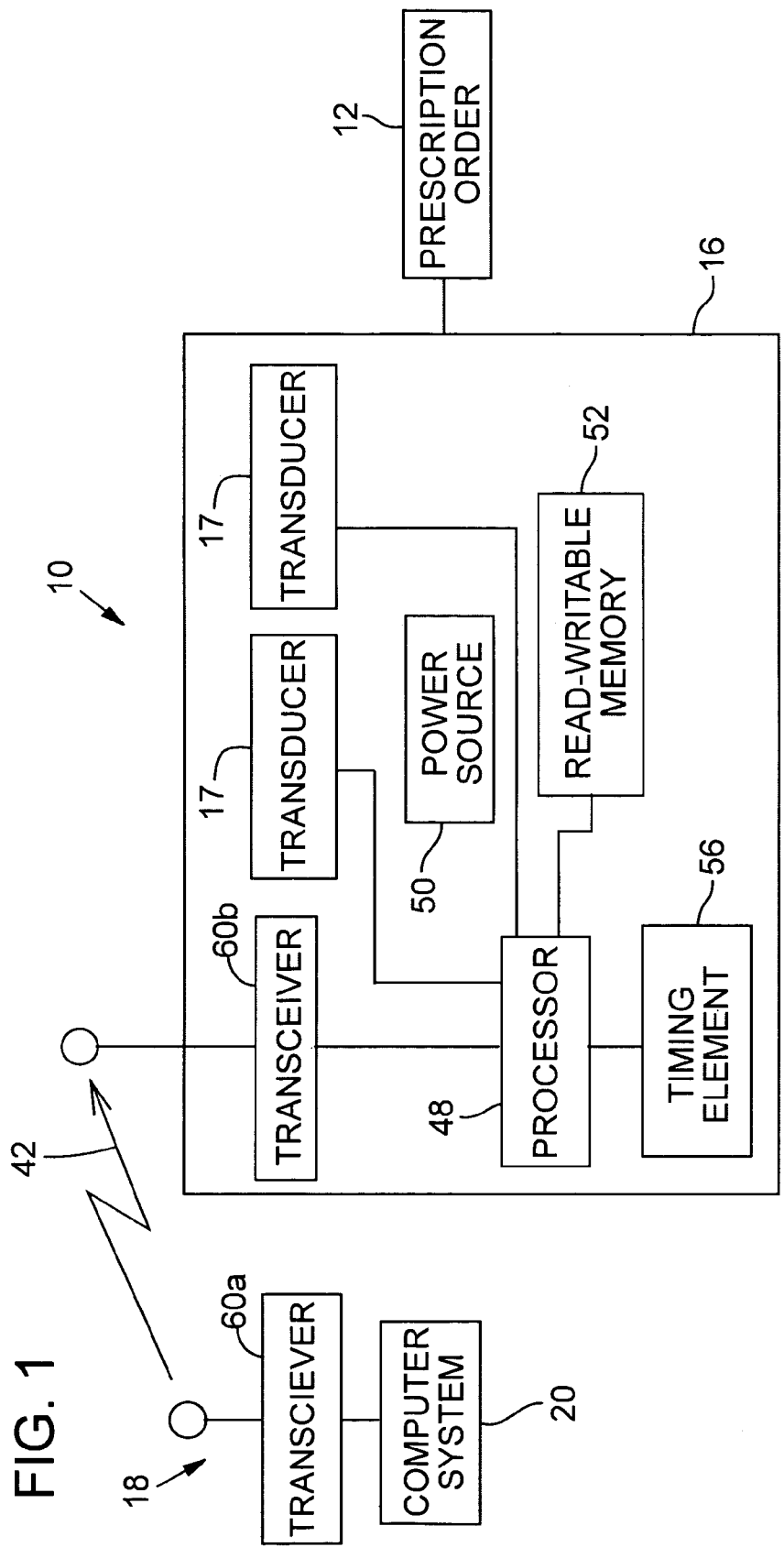
FIG. 1 is a schematic diagram of an identification tag in accordance with an embodiment of the present invention.

FIG. 1 discloses an exemplar tag 16 and related components for locating a prescription order 12 in a pharmacy 14. The computer system 20 is operably connected to a transceiver 60a, such as for example, a conventional Radio-Frequency Identification ("RFID") tag, that transmits a signal 42 to a plurality of tags 16. Each tag 16 is assigned to travel with a unique prescription order 12, and includes a transceiver 60b for receiving the signal and internal circuitry such as a processor 48, power source 50 and memory 52 which contains a unique identifier for that tag and control logic to preferably activate one or more transducers 17, which serve as the worker signaling device when the tag 16 receiving a unique signal 42 from the transmitter 40. Such transducers 17 may also be operably secured to the tag reader 18 or some other structure as needed to assist a worker.

Figure 4:
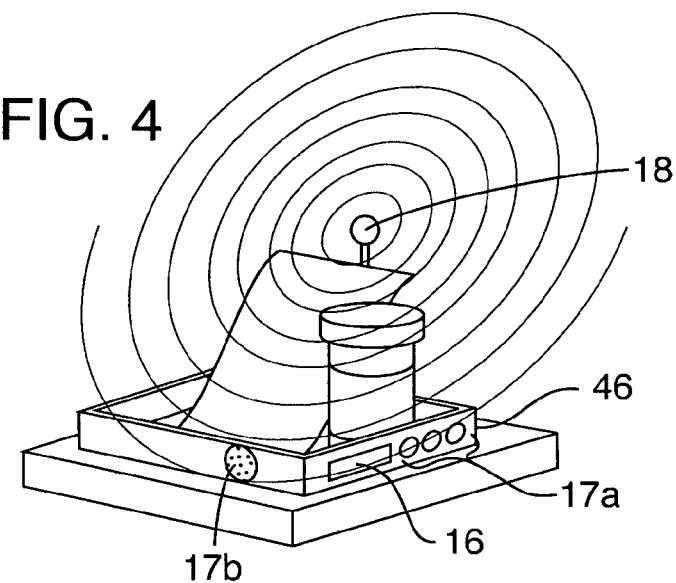
FIG. 4 is an isometric view of a prescription order having a tag operably secured thereto with the tag having a plurality of transducers thereon.

Preferably, the transducer 17 are either a light 17a (FIG. 4) or audio speaker 17b (FIG. 4). More preferably, there are a plurality of transducers 17 that can be individually activated on each tag 16. For example, there can be three lights of different colors (i.e. red, yellow, and green), which can be activated either alone or in combination to identify the status of that prescription order 12. With a different status being denoted by a different transducer being activated.

More preferably, the memory 52 on the tag is read-writable that is preferably coded with key information about the prescription order and or pharmacy supply, such as the customer's name, identifying information, date of birth, social securing number, prescription number, proper storage instructions, known side-effects, expiration date, prescribed drug, insurance information, directions for use, National Drug Control ("NDC") number, and the like.

Also, the computer system preferably monitors these parameters and compares them to a known database of relevant information to alert a worker if a particular pharmacy supply should no longer be dispensed. For example, the computer system preferably uses this tracked information to alert a worker if a pharmacy supply has expired, been recalled, lost its Federal Drug Administration ("FDA") approval, or the like.

The computer system 20 includes appropriate application programs 136 (FIG. 7) and memory 122 (FIG. 7) to correlate a customer's identifying information such as their name, phone number, and the like, with the unique identifier and/or other information in the memory of the tag traveling with that prescription order. Accordingly, when a pharmacy worker wishes to locate a customer's prescription order, he or she may find the customer's identifying information on the computer system 20, and cause the computer system to transmit the unique signal 42 through the transceiver 60a to wirelessly activate one or more transducers 17 on the tag 16 associated with the customer's prescription order 12. For example, the tag's audio speaker 17b may make an audible sound, or one or more lights 17a on the tag 16 may light and/or blink.

Preferably, a plurality of fixed or handheld transceivers, which are collectively referred to as tag readers 18 herein, are spaced apart from each other and positioned at desired locations within the pharmacy 14 to define spaced-apart interrogation zones within the pharmacy. Each tag reader 18 includes a front-end transmitter 62 that generates a digitally encoded signal 64. Preferably, the signal 64 is chosen to facilitate a response from only one uniquely coded tag 16. The receiver portion 66 of the tag reader 18 can induce a coded signal detector that senses the transponder signal 64 and correlates it with a stored code to identify that the tag 16 is present in a particular interrogation zone, thereby also determining the tag's location within the pharmacy.

The computer system 20 can also use conventional triangulation techniques to determine the location of the tag within the pharmacy. In which case, only two spaced-apart tag readers 18 need be placed within the pharmacy. Alternatively, using quasi-sonar-type locating techniques, a single tag reader 18 could be used determine the location of the tag within the pharmacy.

Each tag 16 can be either passive or active. In the passive mode, the tag circuitry accumulates and then returns a signal, if the interrogation signal matches a predefined code sequence stored in memory in the tag's circuitry. In an active mode, each tag further includes a power source 50 that assists with signal amplification, detection and/or wave forming.

B. Prescription Supply Tracking

Tags 16 may also be used to track the location of the prescription orders and prescription supplies 13 as they travel throughout the pharmacy 14 and an off-site facility 15. For example and referring to FIG. 5, a prescription order 12 is presented to the pharmacy 14 and assigned an identification tag 16, preferably with one or more transducers 17 thereon. Tag readers 18 are positioned at key locations throughout the pharmacy 14 and in communication with the computer system 20 having a display 22, such that the movement of the prescription order 12 throughout the pharmacy 14 automatically detects and records the location of the tag 16 without further worker input. In addition to, or alternatively, the transducers 17 can be operably secured to a tag reader 18 or some other object.

Accordingly, a worker can easily determine the location of the prescription order 12 and/or prescription supply 13 within the pharmacy by entering commands in the computer system 20 with a user input device such as a keyboard 120 to display the location of the prescription order 12 and/or prescription supply 13 on the computer display 22. Alternatively, the computer system can detect the identity of a customer based on predetermined criteria such as by detecting a tag operably secured to the customer, or through bio-medical detection techniques such a retina or fingerprint scanning, and initiating retrieval of the detected customer's prescription order.

Each tag reader 18 is placed in communication with the computer system such that information regarding the customer, his prescription order position, and the status of his order can be readily displayed on the computer display 22, and thereby facilitates location of the prescription order 10 within the pharmacy 14.

Preferably, the identification tags 16 are attached to the prescription label, detachably secured to the prescription order, or rigidly secured to a carrier 46 (FIG. 4) containing these documents and other materials related to filling the prescription. Tags 16 are also preferably operably secured to pharmacy supply containers and the like. The tags themselves can be either rigidly or detachably secured to the prescription order and/or pharmacy supplies. For example, the tags can be directly secured to the prescription order and/or pharmacy supply container with adhesive or secured within a lid. Also, the tags can be secured to a fastener, such as a paperclip, that is detachably secured to the prescription order.

1. Pharmacy Prescription Order Filling Procedure

Referring specifically to FIG. 6, an exemplary pharmacy, which is preferably a retail pharmacy, prescription order filling procedure is disclosed. In step P1, a prescription order, which could include a written prescription form, a renewable prescription label, or any other tangible medium documenting a request for a prescription by a health care provider is presented to the pharmacy either in person, via facsimile, via phone, or via a computer transmission, such as e-mail. A pharmacy worker then reviews the prescription order and attaches a unique tag 16 (FIG. 4) to it that is readable by a tag reader 18 (FIG. 4) to determine its location within the pharmacy 14.

As shown in Step P2, the pharmacy worker then determines if the prescription order is for a new prescription. If not, the worker determines if the prescription is refillable (Step P5). If the prescription is not refillable, the pharmacy worker will typically contact the physician or the physician's office to determine if the prescription should be refilled (Step P6). If the physician denies a refill, the customer is informed (Step P12). If the physician does not answer the customer is notified and the pharmacy typically holds the prescription order until the physician calls back (Step P 13).

If the pharmacy worker ultimately determines that the prescription order is fillable, by the answers to any of Steps P2, P5, or P6 being affirmative, the pharmacy worker then must typically determines if the prescription order is able to be sent to a remote filling facility or if it will be filled onsite within the pharmacy itself (Step P20).

A. Onsite Filling of Prescription Order

If the pharmacy worker determines that the prescription order is to be filled onsite, he or she first conducts an initial review (Step P3) which includes checking the available inventory for the prescribed drug (Step P4), determining if there is available insurance (Step P7) and if required, obtaining approval from the insurer and preparing the label and necessary billing and information disclosure paperwork (Step P8).

Regarding Step P4, if the inventory is not in stock, the pharmacy worker typically informs the customer and offers the customer an opportunity to special order the prescribed drug (Step P14). If there is only a partial amount of the prescribed drug in stock, the pharmacy worker will typically initiate a procedure for filling only a partial order (Step P15). This procedure typically includes preparing additional paperwork to alert the customer that only a partial order has been filled, and ordering additional quantities of the prescribed drug.

Regarding Step P7, if the insurance coverage is denied, the prescription order is typically held in an area pending the customer being contacted to request authorization to proceed (Step P16). If the insurer cannot be contacted, the pharmacy has the option to either fill the prescription and alert the customer upon pick-up, or hold the prescription order pending a response from the insurer (Step P17).

After the initial review is complete, the prescription order and related paperwork is presented to a technician for data entry (Step P8) and filling (Step P9), the technician fills the prescription order and attaches the label. The technician then presents the filled prescription order and related paperwork to a registered pharmacist for verification (Step P10).

Following verification, the filled prescription is placed in a storage area pending customer pick-up (Step P11).

B. Filling at Remote Filling Facility

Figure 2:
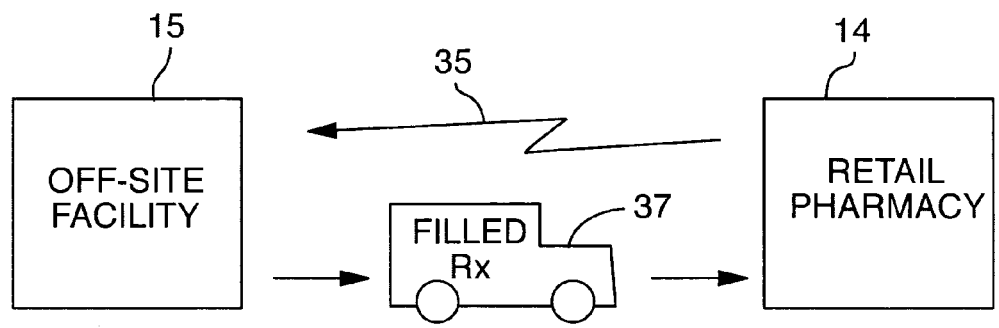
FIG. 2 is a schematic diagram of an exemplar retail pharmacy using a remote filling station to fill one or more prescription orders, and return the filled prescriptions to the retail pharmacy for distribution.

If in Step P20, the pharmacy worker determines that the prescription order should be filled at an off site remote facility, the prescription order is transmitted to an off-site facility, usually electronically as shown in FIG. 2. In such case, the remote filling facility will attach a new tag to the prescription order, and if equipped with one, may code the tag's read-writable memory 52 (FIG. 1) with appropriate drug identifying and other information about the prescription order.

At the remote filing facility, the prescription order is filled in compliance with traditional filling practices, procedures and regulations, including conducting an initial review, checking insurance, labeling, data entry, filling, and verification (Step P21). The filled prescription order is then combined with other filled prescription orders to be delivered to the pharmacy and transported essentially in bulk to the pharmacy as shown in FIG. 2.

Figure 3:
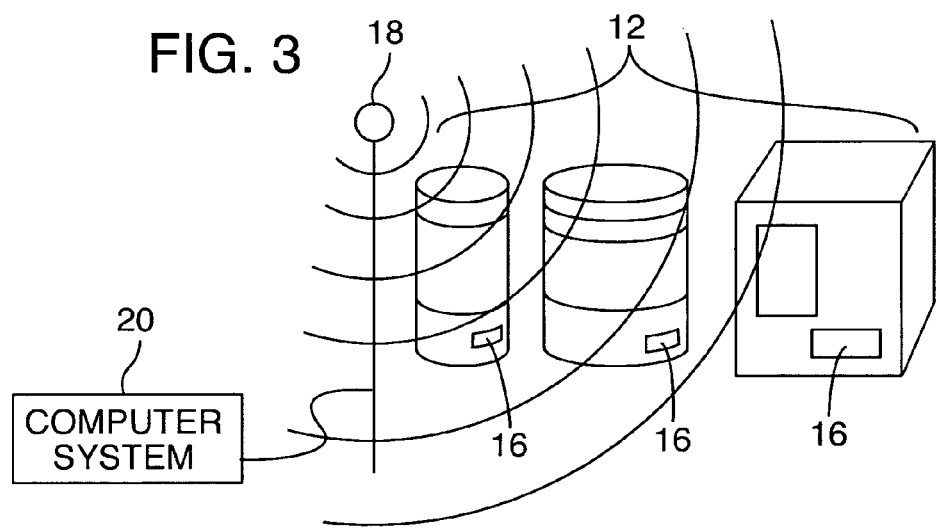
FIG. 3 is an isometric view of simultaneous scanning of a plurality of supply containers in accordance with an embodiment of the present invention.

Upon arrival at the pharmacy, the bulk shipment of filled prescription orders are preferably positioned in bulk within an interrogation zone of the computer system (Step 22), which simultaneously reads the tag 16 on each prescription order in the bulk shipment as shown in FIG. 3, and updates the computer system's records with this information, including any new information added by the remote filling facility to the tag's memory 52 (FIG. 1). Each filled prescription is then placed in a storage area with prescription orders that were filled on-site pending customer pick-up (Step P11).

When a customer picks-up his or her filled prescription, the pharmacy worker complies with applicable customer notice requirements, and obtains the customer's signature (also called "signature capture") confirming that they have received such notice (if applicable) and that they have received the filled prescription (Step P18).

2. Pharmacy Tracking Zones

In practice and referring specifically to FIG. 5, it is more efficient to perform the various steps noted above at spaced apart locations, or zones, throughout the pharmacy. For example, prescription order intake (Step P1 of FIG. 6) and initial review (Step P3 of FIG. 6) can be performed at location 21 (FIG. 5). Label printing and data entry (Step P8 of FIG. 5) could be accomplished at location 27 (FIG. 5). Prescription orders waiting from some form of call back either from the customer, the insurer, or the health care provider could be placed at location 27 (FIG. 5). Orders waiting to be filled could be placed at location 28 (FIG. 4), orders waiting pharmacist review and approval could be place at location 23 (FIG. 4), and approved filled prescription orders could be stored at location 30 (FIG. 4). Obviously, additional zones (24 & 28) could be added to accommodate a particular pharmacy's practices and procedures.

Preferably each station includes a tag reader 18 in communication with the computer system 20 for automatically detecting the arrival of the tag 16 attached to the prescription order 12 and or the pharmacy supply as it enters each location. More preferably, the tag reader 18 detects both the arrival of the tag 16 in that station, and the departure of that tag 16 from that station, with the time interval at that station being determined and recorded therefrom.

Each tag reader 18 is preferably fixed at a particular location so that detecting the presence of a tag near the device also automatically indicates the location of that tag 16 within the pharmacy. The tag readers 18 can be rigidly mounted to a work area or station, or portable (i.e. handheld) devices that are operably connected to the station so that it can indicate a location within the pharmacy of a detected tag. Such portable devices facilitate scanning of prescription orders that are compiled in bulk, such as a container of filled prescriptions arriving from an off-site filing facility (Step P22, FIG. 6). Since each prescription order in the container has a unique tag 16 the tag reader 18 can simultaneously detect and record the location of multiple prescription orders, a pharmacy worker can wave the tag reader 18 over the container to record the location of all prescription orders in the container and obtain information recorded in the read-writable memory of each tag.

3. Storage Bin

Figure 14:
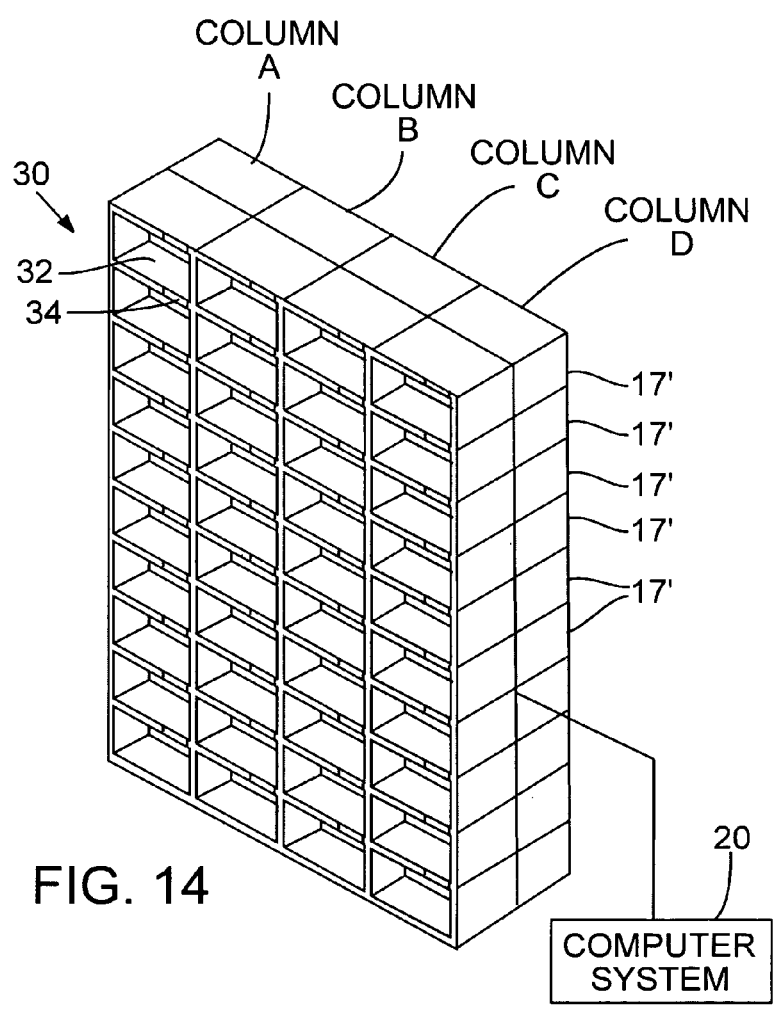
FIG. 14 is a front, isometric view of a storage structure having a plurality of antenna array cards operably secured thereto.

Space and efficiency can be optimized by storing pharmacy supplies used by the pharmacy in a supply storage bin 30 and/or filled prescription orders 12 to be held for pick-up into a common will-call storage bin 30'. As best shown in FIGS. 14-16, the storage bins 30, 30' each includes a plurality of cubbies 32, with each cubby 32 being sized to receive a prescription order 12 and/or a pharmacy supply container therein. Each cubby is uniquely identified 34, such as by being individually numbered, and includes a tag reader 18, which is preferably an economical antenna or the like operably secured to a common tag reading device by a switching device 36 (which is also commonly known as a multiplexer) for determining whether a particular tag 16 is received within it. Each tag reader 18 is preferably periodically in communication with the computer system 20.

When a supply container is returned to the supply storage bin 30, it is simply inserted into an available cubby 32. Accordingly, the tag reader 18 associated with that cubby 32 sends a signal to the computer system 20 denoting the particular location and cubby number where the pharmacy supply is held. When a pharmacy worker seeks that particular pharmacy supply in the future, the worker enters the pharmacy supply's identifying information into the computer system 20, and the particular bin number of the cubby containing the pharmacy supply is displayed. The worker then locates and removes the pharmacy supply from the identified cubby.

Alternatively, and/or in addition to determining the cubby number in which the customer's filled prescription order is located, the computer system can activate one or more transducers 17 positioned near the filled prescription order or on the tag 16 secured to the prescription order to alert the worker of its location.

The removal of the pharmacy supply from that particular cubby 32 is detected by the tag reader 18 and reported to the computer system 20. The tag 16 can remain affixed to the pharmacy supply when used, thereby allowing it to be easily located and retrieved in the future.

4. Storage Cart

Figure 20:
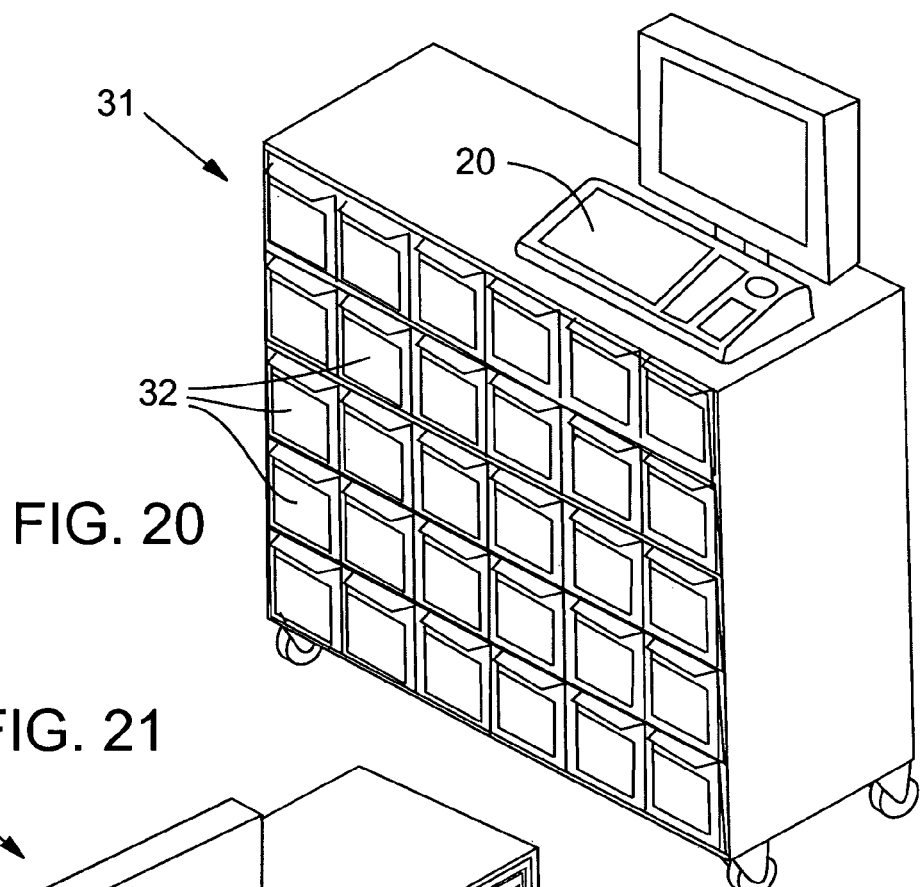
FIG. 20 is a front, isometric view of a portable prescription supply container storage cart in accordance with an embodiment of the present invention.
Figure 21:
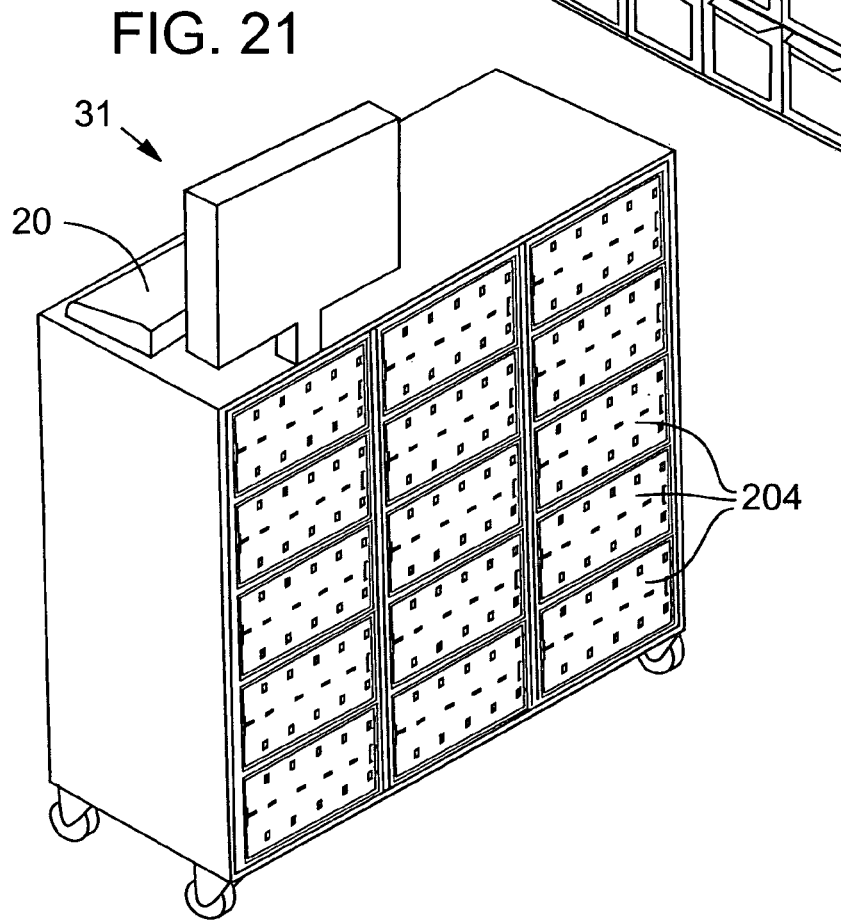
FIG. 21 is a rear, isometric view of the portable prescription supply container storage cart in accordance with an embodiment of the present invention.

As best shown in FIGS. 20 & 21, the storage area 30 having a plurality of bins 32 therein can also be made portable, such as by placing it on wheels or casters, thereby defining a portable prescription supply storage cart 31 that may be wheeled throughout the pharmacy to allow easy access to a pharmacy supplies contained therein.

Preferably, the portable prescription supply storage cart includes a source of power, such as a battery or the like, an input device such as a mouse and/or keyboard, and a portable tag reader 18 and monitor in communication with the computer system. Accordingly, the cart serves as a stand-alone structure for allowing a worker to easily locate a particular prescription supply within a particular bin and administer the filled prescription to the correct patient.

The computer system detects the presence and removal of a tagged pharmacy supply and/or prescription order, thereby allowing for the easy location of the tagged item. For example, transducers, such as lights and speakers, on the cart and adjacent to the bins can activate to direct a worker to the correct bin containing a desired item.

It can be appreciated that the present system offers several benefits. For example, it allows or real time inventory control of pharmacy supplies, and it contributes to reducing the amount of pharmacy supply "shrink." It can also be used to prevent expired, recalled, or other drugs that should not be dispensed from actually being dispensed to a customer or the like. Also, it allows a worker to easily locate any pharmacy supply within the pharmacy, even if it has been misplace by another worker or is currently being used by another worker.

c. Storage Bin Locking Structure

Figure 22:
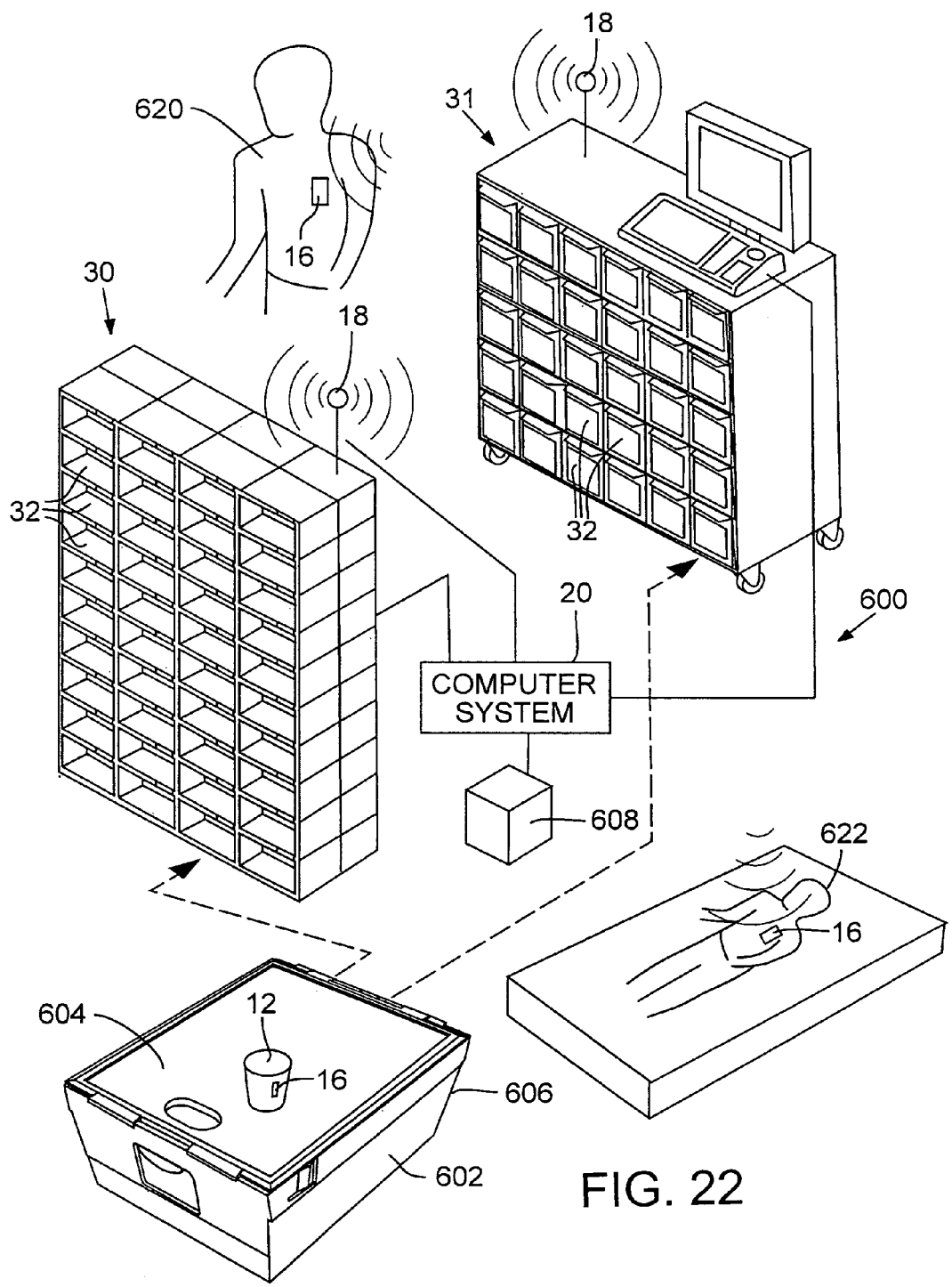
FIG. 22 is an exemplar prescription supply container storage cart and storage cabinet locking system in accordance with an embodiment of the present invention.

As shown schematically in FIG. 22, each bin, either in the storage structure 30 or the cart 31 preferably includes a locking structure 600 in communication with the computer system 20 to limit access to filled prescription orders 16 or pharmacy supplies 17 placed therein. For example, a locking tray 602 can operably receive a container 604 having the filled prescription 12 thereon. The tray 602 is sized to secure the container 604 therein and to be slidably received within a bin 32. One or more hooks 606 preferably extend from the tray. The hooks 606 operably engage an electric lock 608 received within or near the bin 32 thereby locking the tray 602 within the bin 32. Accordingly, with the tray 602 locked to the lock 608 within the bin 32 and the container 604 secured within the tray 602, the container 604 cannot be removed from the bin 32.

The electric lock 608 is in communication with the computer system 20 that controls the lock 608 so as to only unlock the tray 602 from the lock 608 when predetermined criteria are met. For example, a worker 620 can wear an identification tag 16 that is detected by a tag reader 18 placed near the bin 32 in which the worker 620 seeks to unlock. The computer system 20 first verifies that the worker 620 is authorized to have access to the items the locked bin, and opens the lock 608 only if the detected worker 620 is authorized. This locking system allows commonly prescribed medications, which are often referred to in the industry as "top 100" medications, to be securely stored within a healthcare facility, but also remain easily accessible to authorized workers, particularly during times when the pharmacy is closed.

C. Computer System

Those skilled in the art will appreciate that an exemplary embodiment of the present invention relies on and incorporates several common features of modern personal computers. The general use, operation, and construction of a computer system is known and has been disclosed in numerous patents such as U.S. Pat. No. 5,818,447 to Wolf et al. and U.S. Pat. No. 5,752,025 to Shakib et al.

Referring to FIG. 6, the following discussion is intended to provide a brief, general description of a suitable computing environment in which the invention may be implemented. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

With reference to FIG. 6, an exemplary system for implementing the invention includes a general purpose computing system in the form of a conventional personal computer 20, including a processing unit 121, a system memory 122, and a system bus 123 that couples various system components including the system memory to the processing unit 121. The system bus 123 may be any of several types of bus structures including a memory bus or memory controller, a peripheral bus, and a local bus using any of a variety of bus architectures. The system memory includes read only memory (ROM) 124 and random access memory (RAM) 125. A basic input/output system 126 (BIOS), containing the basic routines that help to transfer information between elements within the personal computer 20, such as during start-up, is stored in ROM 124. The personal computer 20 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of computer readable instructions, data structures, program modules and other data for the personal computer 120. Although the exemplary environment described herein employs a hard disk, a removable magnetic disk 129 and a removable optical disk 131, it should be appreciated by those skilled in the art that other types of computer readable media which can store data that is accessible by a computer, such as magnetic cassettes, flash memory cards, digital video disk, Bernoulli cartridges, random access memories (RAMs), read only memories (ROM), and the like, may also be used in the exemplary operating environment.

A number of program modules may be stored on the hard disk, magnetic disk 129, optical disk 131, ROM 124 or RAM 125, including an operating system 135, one or more application programs 136, other program modules 137, and program data 138. A user may enter commands and information into the personal computer 20 through input devices such as a keyboard 140, pointing device 142, and tag readers 18. Other input devices (not shown) may include a microphone, joystick, game pad, satellite dish, scanner, or the like.

These and other input devices are often connected to the processing unit 121 through serial port interface 146 that is coupled to the system bus, but may be connected by other interfaces, such as a parallel port, game port or a universal serial bus (USB). A display 22 or other type of display device is also connected to the system bus 123 via an interface, such as a video adapter 148. In addition to the monitor, personal computers typically include other peripheral output devices (not shown), such as speakers and printers.

The personal computer 20 may operate in a networked environment using logical connections to one or more remote computers, such as a remote computer 149. The remote computer 149 may be another personal computer, a server, a router, a network PC, a peer device, a personal digital assistant ("PDA"), or other common network node, and typically includes many or all of the elements described above relative to the personal computer 20, although only a memory storage device 150 has been illustrated in FIG. 7. The logical connections depicted in FIG. 7 include a local area network (LAN) 151 and a wide area network (WAN) 152. Such networking environments are commonplace in offices, enterprise-wide computer networks, intranets and the Internet.

When used in a LAN networking environment, the personal computer 20 is connected to the local network 151 through a network interface or adapter 153. When used in a WAN networking environment, the personal computer 20 typically includes a modem 154 or other means for establishing communications over the wide area network 152, such as the Internet. The modem 154, which may be internal or external, is connected to the system bus 123 via the serial port interface 146. In a networked environment, program modules depicted relative to the personal computer 20, or portions thereof, may be stored in the remote memory storage device. It will be appreciated that the network connections shown are exemplary and other means of establishing a communications link between the computers may be used.

Preferably, a plurality of networked personal computers 20 are positioned within the pharmacy, one at the intake area (21, FIG. 5), one at the customer pick-up area (29, FIG. 5), and one at the data entry/label area (27, FIG. 5).

D. Multiplexing Tag Reader Array

Referring to FIGS. 5 and 8-17 a plurality of tag readers 18, which are distributed throughout the pharmacy 14, are preferably integrated with a switching device 36 that periodically monitors the status of each tag reader 18 and transmits that information to the personal computer 20.

Figure 8:
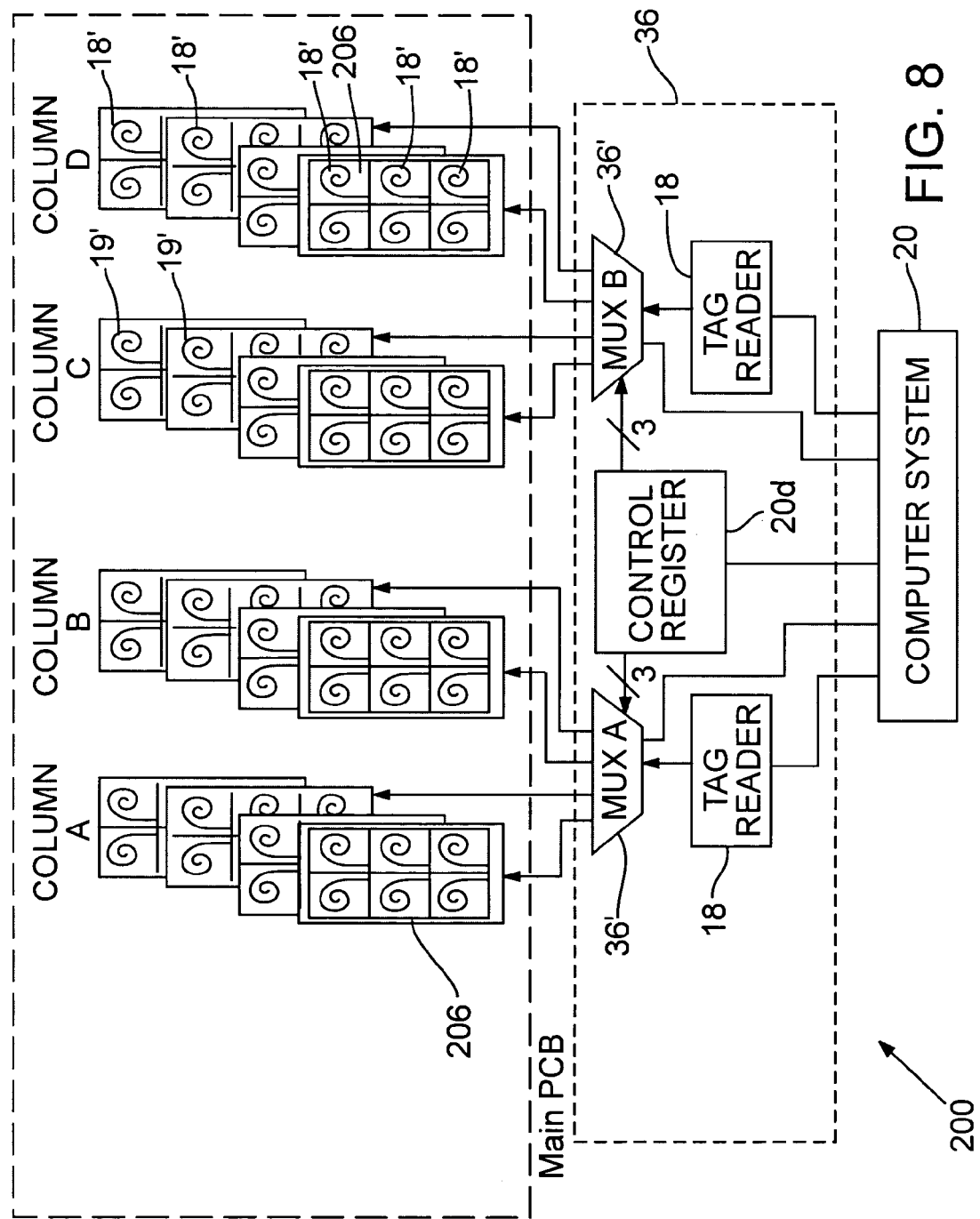
FIG. 8 is an exemplar schematic diagram of a multiplexed tag reader array and related system in accordance with an embodiment of the present invention.
Figure 9:
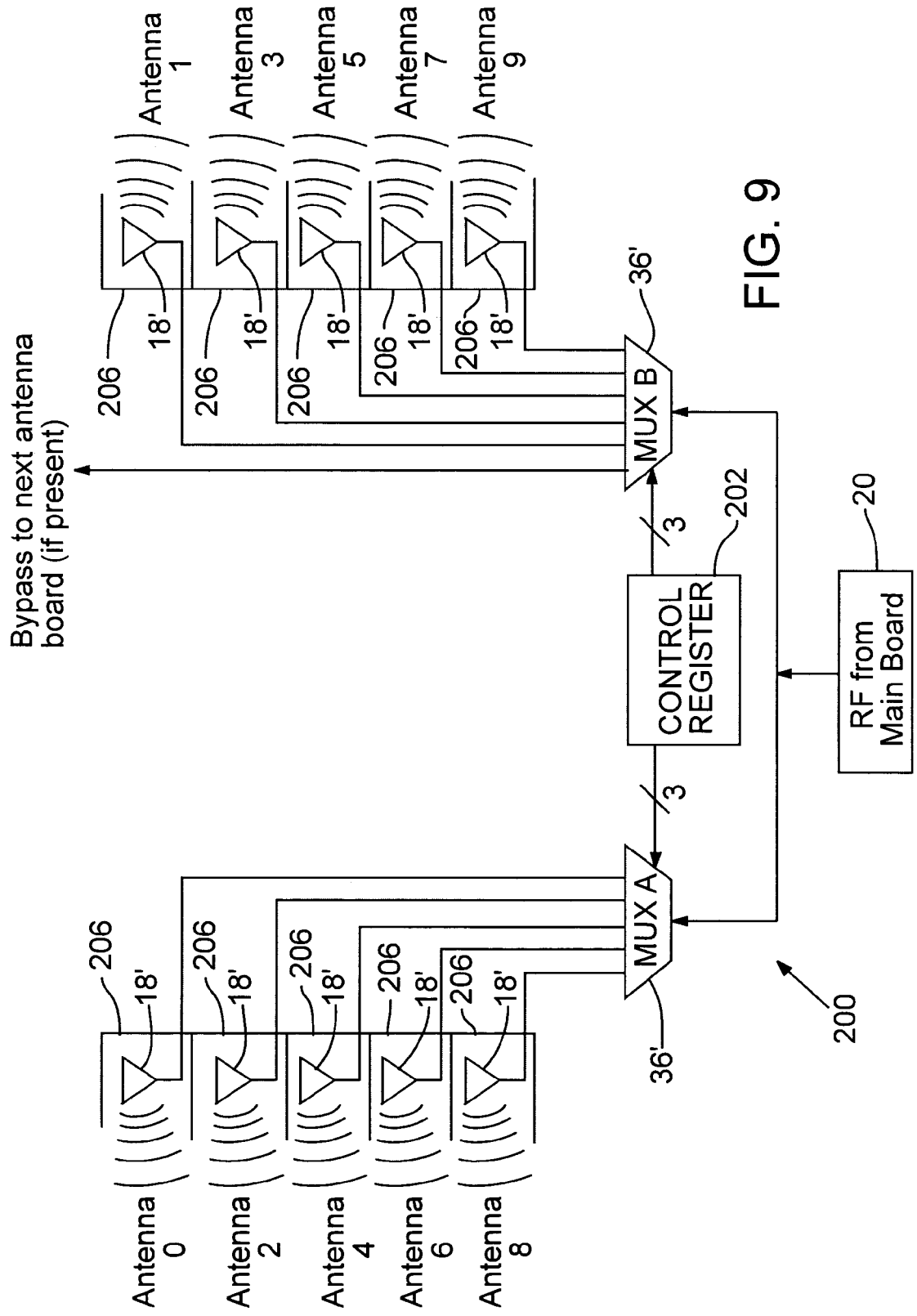
FIG. 9 is an alternative exemplar schematic diagram of a multiplexed tag reader array and related system.
Figure 12:
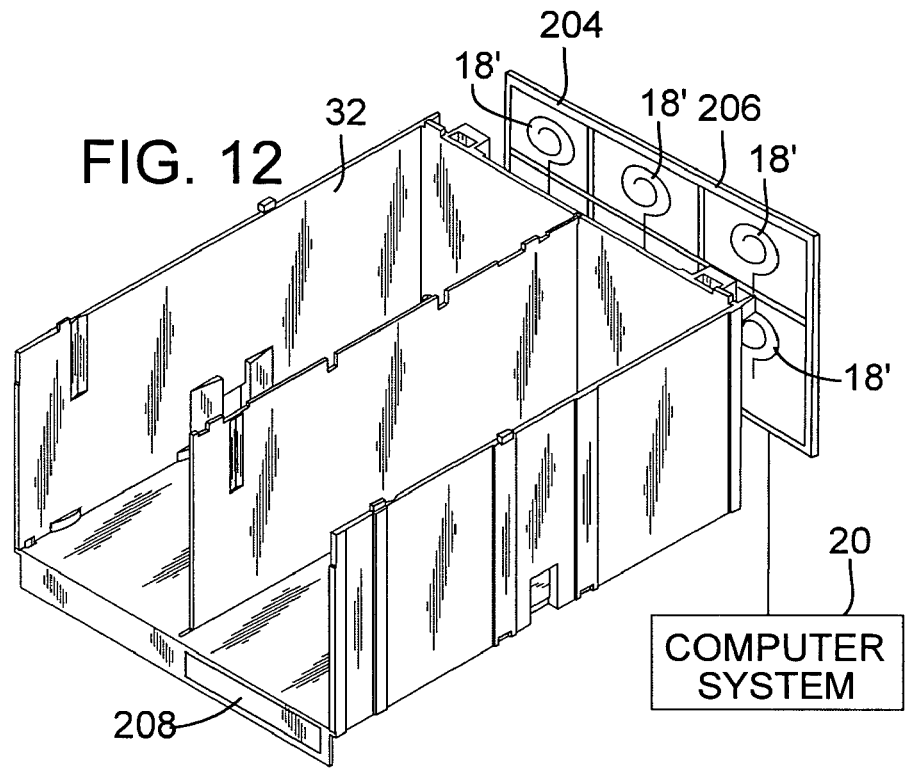
FIG. 12 is a front isometric, exploded view of a storage bin having an antenna array card operably secured thereto.
Figure 13:
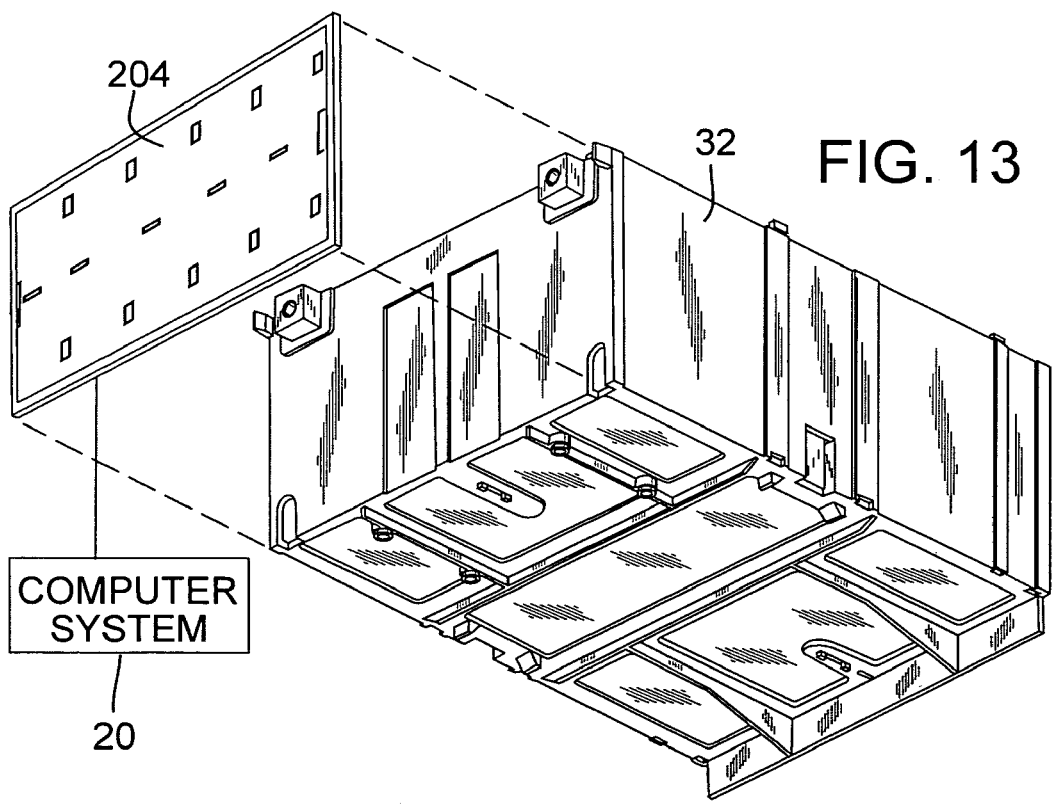
FIG. 13 is a rear, isometric, exploded view of the storage bin and antenna array card of FIG. 12.

An exemplar multiplexing system 200 is disclosed in FIGS. 8 & 9. Preferably, the antenna 18' of each tag reader 18 is operably secured to a multiplexer 36'. Such multiplexers 36' are commonly known to those skilled in the art. A plurality of antenna 18' are operably secured to the multiplexer 36' such that the multiplexer 36' connects each antenna 18' one-by-one to the tag reader 18. Each antenna 18' is positioned at a specific location within the pharmacy 14. For example, one or more antenna 18' can be positioned adjacent to a particular work area 97 upstream of the storage area 30, or can be positioned adjacent to a particular cubby 32 in the storage area 30. A control register 202 monitors which antenna 18' is connected to the tag reader 18 at a given time and provides this information to the computer system 20, which also detects a tracking signal from the tag reader 18 to determine the presence and a tag and thereby determine its location within the pharmacy 14.

Preferably, and as best shown in FIGS. 10-13, a plurality of antenna 18' are formed onto a substantially planar frame 204 with a signal shielding structure 206 encircling one or more antennas 18'. For example, the antenna 18' can be a coil aligned on the planar frame 204 and the signal-shielding structure 206 can be a short circuit encircling the coil on the planar frame 204. Accordingly, the interrogation field of the antenna 18' is directed substantially perpendicular to the planar frame 204. Accordingly, a large number of antenna 18' can be concentrated within a small area, say for example, in a will-call storage device, with each antenna detecting the presence of a tag only if placed within a cubby immediately adjacent to the antenna 18'. Alternatively, the shielding structure can be an electrically grounded frame that surrounds an area in which an interrogation field of a tag reader is directed.

Preferably, the tags operate at a relatively low frequency band of around 13.56 megahertz (MHz). This frequency has been found to allow a plurality of tags within a small area to each be detected by a common tag reader. Moreover, tags operating at about this frequency are able to penetrate through liquids and other materials commonly found in a pharmacy without adversely affecting the tracking performance of the tag.

Although less desirable, the tags operating at an ultra-low frequency such as in the range of about 125 kilohertz (kHz) to about 134.2 kilohertz (kHz) or in the ultra-high frequency band of between about 860 megahertz (MHz) to 960 megahertz (MHz) can also be used.

Figure 17A:
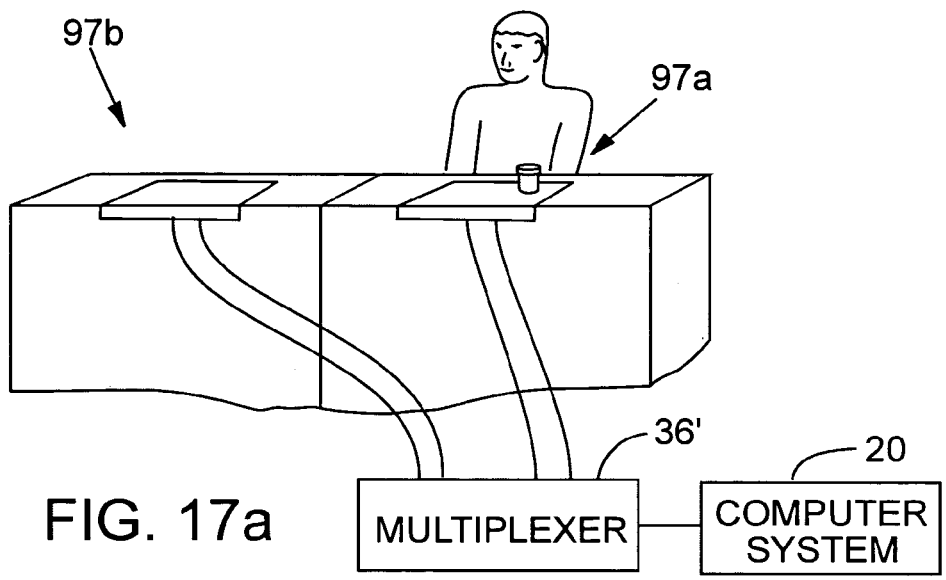
FIG. 17a is an exemplar, isometric view of a possible workstation having a substantially horizontally mounted planar frame containing at least one tag reader antenna therein.
Figure 18:
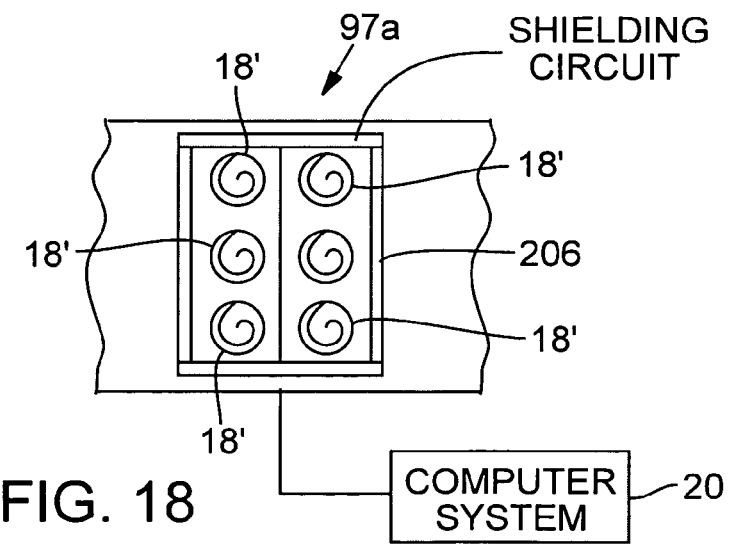

Alternatively, the planar frame 204 containing one or more antenna 18' may be positioned substantially horizontally on a work area 97a, 97b as shown in FIGS. 17a, 17b & 18 with the fields of the antenna directed substantially upward (FIG. 17a) or downward (FIG. 17b). In such case, the signal shielding structure 206 need not necessarily encircle each individual antenna 18' on the frame 204 as shown in FIG. 10. Rather, if needed the shielding structure 206 can encircle the entire frame 204 as best shown in FIG. 18 thereby defining a particular work area 97a and preventing the antenna 18' from inadvertently detecting the presence of a tag in an adjacent work area 97b.

Moreover, and referring to FIGS. 19a & 19b, a plurality of antenna can be positioned around a scanning area and all directed within that area to form a defined space or tunnel 600 in which tags placed therein are scanned by signals generated from a plurality of antenna. Such a scanning tunnel allows for more accurate detection of all tags, particularly when a plurality of tags are grouped together, such as in a bulk shipment received from a remote pharmacy or other off site location.

If desired, the exterior of the storage area can include transducers 17' thereon, such as lights, speakers, or the like that are in communication with the computer system to alert a worker of the location of a particular prescription order. Similarly, each cubby of the storage device can also include transducers 17' thereon to perform a similar function.

In view of the wide variety of embodiments to which the principles of the invention can be applied, it should be apparent that the detailed embodiments are illustrative only and should not be taken as limiting the scope of the invention. For example, the computer system can correlate a particular "read only" code on a tag with one or more aspects of the prescription order and/or person to which it is associated with, and use this correlation throughout the tracking system. Rather, the claimed invention includes all such modifications as may come within the scope of the following claims and equivalents thereto.

We claim:

1. A prescription supply container tracking system for use in a retail pharmacy having a first station therein for filling the prescription order and a storage device for holding supply containers therein when not in use; said tracking system including:

a computer system having a display;

a tag operably secured to the prescription supply container; and a first tag reader positioned near the first station in the retail pharmacy and in communication with said computer system, said first tag reader able to automatically detect the presence of said tag when said tag is moved by hand to a position in close proximity of said first tag reader and send a first signal to said computer system;

such that said computer system automatically detects said first signal and automatically processes said signal under control of said computer system to display the presence of said tag at said first station within the retail pharmacy, thereby displaying the location of said prescription supply container;

said storage device includes:

a storage bin having a plurality of cubbies, each said cubby having an individual identifier, and having a cubby tag reader in communication with said computer system, such that the presence of said tag within one of said plurality of cubbies is automatically detected by that cubby's tag reader and sends a cubby location signal to said computer system, said cubby location signal including the individual identifier of said one of said plurality of cubbies;

such that said computer system processes said first signal and said cubby location signal to display the location of said tag at one of said first location or said one of said plurality of cubbies thereby allowing the location of said supply container within said storage device; and wherein said computer system determines the identity of the supply container sought by a pharmacy worker and verifies that said supply container removed from the storage device is the same as the identity of the supply container sought by the pharmacy worker.

2. The prescription order tracking system of claim 1, further including:

a second station spaced apart from said first station; and wherein said second station has a second tag reader positioned within the retail pharmacy and in communication with said computer system, said second tag reader able to automatically detect the presence of said tag when said tag is moved by hand to a second position in close proximity of said second tag reader and send a second signal to said computer system;

such that said computer system automatically detects said second signal and automatically processes said first signal and said second signal to display the location of said tag at one of said first and second stations within said retail pharmacy, thereby displaying the location of said prescription supply container.

3. The prescription supply container tracking system of claim 1, wherein the computer system alerts the pharmacy worker if the supply container removed from the storage device is different from the identity of the supply container sought by the pharmacy worker.

4. The prescription supply container tracking system of claim 3, wherein the computer system correlates expiration date information about the material within the supply container with the supply container; and verifies that the expiration date has not passed when the supply container is removed from the storage container.

5. The prescription supply container tracking system of claim 4, wherein said computer system alerts a pharmacy worker if the expiration date has passed.

6. The prescription supply container tracking system of claim 1, wherein said tag is a radio frequency identification tag and said tag reader is a radio frequency identification tag reader.

* * * * *